United States Patent [19]

McNulty

[11] Patent Number: 5,417,941

[45] Date of Patent: May 23, 1995

[54] MICROWAVE POWERED STEAM PRESSURE GENERATOR

[75] Inventor: Bernard A. McNulty, Weston, Conn.

[73] Assignee: e/h Technologies, Inc., Weston, Conn.

[21] Appl. No.: 181,004

[22] Filed: Jan. 14, 1994

[51] Int. Cl.⁶ ............................................. A61L 2/06
[52] U.S. Cl. .................................. 422/307; 422/298; 422/292; 219/682; 219/696
[58] Field of Search ................ 422/26, 295, 298, 307, 422/292; 219/682, 687, 688, 695, 696, 750

[56] References Cited

U.S. PATENT DOCUMENTS

| | | | |
|---|---|---|---|
| 560,951 | 5/1896 | Thresh | 422/298 |
| 2,614,027 | 10/1952 | Kollsman | 422/298 |
| 3,753,651 | 8/1973 | Boucher | 422/298 |
| 3,891,817 | 6/1975 | Brown | 219/688 |
| 4,067,683 | 1/1978 | Klaila | 219/687 |
| 4,288,674 | 9/1981 | Counall | 219/687 |
| 4,400,357 | 8/1983 | Hohmann | 422/297 |
| 4,851,630 | 7/1989 | Smith | 219/687 |
| 4,861,956 | 8/1989 | Courneya | 219/696 |
| 4,987,284 | 1/1991 | Fujimura et al. | 219/695 |
| 5,124,125 | 6/1992 | Brent | 422/26 |

Primary Examiner—Robert J. Warden
Assistant Examiner—Theresa T. Snider
Attorney, Agent, or Firm—Edward R. Hyde

[57] ABSTRACT

A portable apparatus which produces high temperature and pressure steam derived from a microwave energy source for the rapid sterilization of medical and dental appliances. Items to be sterilized are placed in a detachable high pressure chamber which is then attached to the microwave powered steam source. Microwave energy is coupled into a guiding structure containing a shaped impedance transformation element so that essentially all of the microwave energy is transferred to a reaction fluid contained in a holder at the end of the matching element. The reaction fluid is rapidly vaporized and the resulting vapors rapidly expand into the chamber through a metal screen that also prevents transmission of microwave energy. Pressure temperature values internal to the chamber are used to control application of microwave power thereby maintaining an optimum micro-organism kill condition for a prescribed time interval.

8 Claims, 2 Drawing Sheets

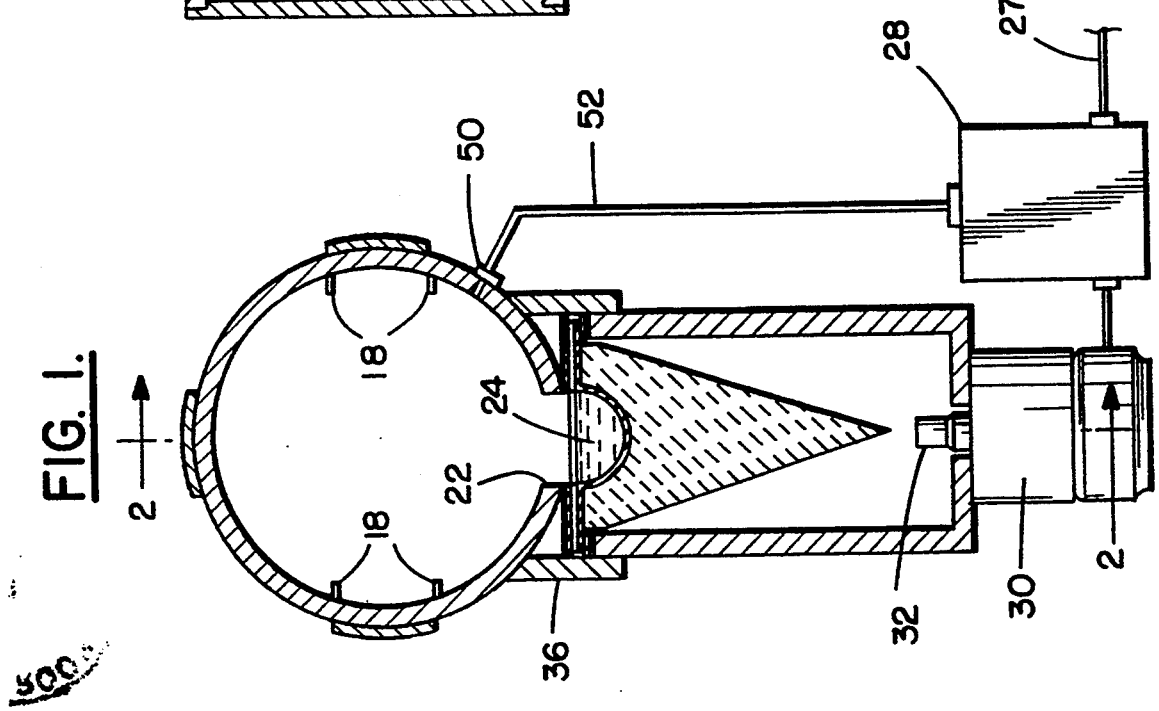

MICROWAVE POWERED STEAM PRESSURE GENERATOR

BACKGROUND OF THE INVENTION

1. Field of the Invention

The present invention relates to a device for sterilizing medical, dental and veterinary appliances, materials and other objects at high temperature and pressure with steam which is produced from a microwave energy source.

Steam sterilizers or autoclaves are well known as applied in the medical field for sterilizing objects such as instruments, tools, and the like. One major problem with current sterilizers is that they require an inordinately large amount of time and energy, and it is to this disadvantage of prior art devices that the present invention serves to overcome. This is accomplished by a unique microwave energy source design coupled to the sterilization chamber resulting in a fast, efficient sterilizing device.

2. Description of the Prior Art

High temperature and pressure steam sterilizers have been well known for many years and are conventionally used in medical and dental establishments for sterilizing the instruments and tools used in medicine and dentistry. Conventionally, the steam results from a supply of reactant liquid such as water that is heated to its boiling point by conventional heating devices such as direct heating elements or infrared sources. Attempts have been made to provide microwave sources for various types of sterilizers. An example of a microwave energy source as sterilizer is found in U.S. Pat. No. 3,753,651 of Boucher. The latter shows in general a household oven type of microwave source for providing energy that irradiates the instruments to kill the bacteria and other micro-organisms. An obvious disadvantage of Boucher is that if the instruments are metallic, as they often are, partial discharge at sharp points will be detrimental and destructive to the instruments.

Another example of a microwave sterilizer is found in U.S. Pat. No. 4,400,357 of Hohmann. This patent contemplates in one embodiment, an IR source for heating the reactant liquid to vaporize it for sterilization of medical instruments. Another embodiment suggests that a microwave source and cavity resonator might be employed in place of an IR source. The patent, however, fails to disclose an efficient coupling between the microwave source and the reactant liquid whereby the latter may be quickly and efficiently vaporized. Without this efficient coupling, the microwave sterilizer of Hohmann would be subject to the time consuming period for vaporization that is found in sterilizers currently in use employing other types of heating elements or result in damage to or destruction of the microwave source.

SUMMARY OF THE INVENTION

The invention provides a compact, efficient device of simple, inexpensive construction for the sterilization of medical, dental and other appliances and materials, and for the processing or digestion of bio-active or toxic matter. Energy requirements for the apparatus are modest and thus it may be operated from the low voltage electrical system of a motor vehicle or other form of transport, thereby allowing its use in un-electrified areas or regions, as well as from modestly sized sources of AC or DC power at a fixed site.

The present invention uses microwave energy to produce high temperature vapor or gas from a liquid reactant. The vapor or gas contacts the objects or matter to be sterilized or processed while held within a prescribed temperature and pressure range for an appropriate amount of time. The apparatus is made up of an inverter type power supply for converting the input electrical power to a form suitable for use with a magnetron or other source of microwave energy, an electromagnetic wave guiding structure which may take any of various shapes, e.g. rectangular, cylindrical, elliptical or multi-axle. A shaped dielectric transition section which may have a linear taper or one of a higher mathematical order, suitable to the geometry of the guiding structure, couples the wave guide to a boat or cavity used to hold a reaction fluid. A metal washer which closes the waveguide and completes the microwave circuit has a perforated center section or screen that will allow the gas or vapor to pass into the sterilization chamber while serving as a barrier to the passage of the microwave radiation. The magnetron, guide section, transition device and seal assembly together thread into a coupling on the high pressure sterilization chamber for holding the objects or materials to be sterilized or processed.

The instruments in the chamber are shielded from microwave energy in order to preclude damage from erosion due to partial discharge brought on by local enhancement of the electromagnetic fields at sharp points and edges of the instruments. Sealed together, the steam generator and cassette form an electromagnetically closed or shielded system which dramatically reduces radiated microwave emissions. Only heated gases and vapors are allowed to fill the chamber in order to perform the sterilization or processing function. Once the chamber and contents have been brought to the optimum temperature and pressure that assure micro-organism killing or processing, pressure or temperature sensor signals from the cassette are used to cause the inverter to control operation of the microwave source. If the internal temperature and pressure of the chamber decline to some preset level, the sensors signal the need to restart the inverter and magnetron, thus providing additional microwave energy for maintenance of the necessary pressure and temperature values for the requisite amount of time. This constitutes a closed loop temperature and pressure regulation means; and therefore optimally efficient operation of the device, as power is only used on an as-needed basis.

Against the foregoing background, it is a primary object of the present invention to provide a sterilizer in which the water is vaporized by a microwave source that is efficient in operation in that a high percentage of the generated microwave energy is coupled to the liquid source resulting in rapid vaporization.

It is a further object of the present invention to provide a unique microwave source of energy especially suitable for coupling to the liquid of a steam-type sterilizer.

It is a still further object of the present invention to provide a device for quickly and efficiently sterilizing medical, dental and other objects and materials by high temperature and pressure steam produced by a microwave energy source.

Another object of the present invention is to provide a steam-type sterilizer operating from a microwave source that serves to vaporize a source of liquid in a fast and effective manner.

BRIEF DESCRIPTION OF THE DRAWINGS

The foregoing and still other objects and advantages of the present invention will be more apparent from the following detailed explanation of the preferred embodiments of the invention considered in connection with the accompanying drawings herein in which:

FIG. 1 is an end sectional view of the sterilizer of the present invention;

FIG. 2 is a section taken along the line 2—2 of FIG. 1;

DESCRIPTION OF THE PREFERRED EMBODIMENT

Figure 3:
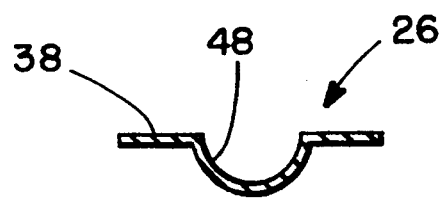
FIG. 3 is a top view of the washer and screen separating the wave guide and water source from the sterilization cabinet.
Figure 4:
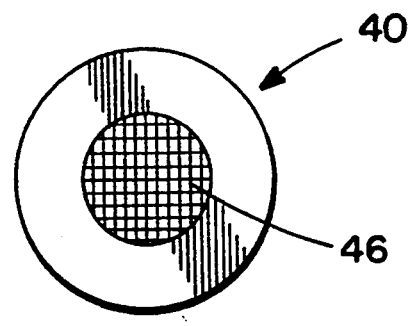
FIG. 4 is a cross-section of the boat or cup used to hold the liquid.

Referring now to the drawings and more particularly Figs. 1 and 2, the system of the present invention includes a microwave energy source system 10 mechanically coupled to a sterilization chamber 12. As will be described hereinafter, the energy source serves to vaporize the reactant liquid to provide vapor under high pressure and temperature within the chamber 12 which holds the instruments or other objects to be sterilized.

The chamber may be of cylindrical shape including a cylinder 13 with a removable end cap 14 adapted to be screwthreaded to the chamber end. The screwthread could be of the fractional turn type to provide rapid and convenient opening and closing of the chamber. A sealing gasket 16 is fitted and tightly held at the end of the container to prevent any venting of vapor during operation. The chamber contains one or more pairs of side rails 18, to support instruments or material carrying trays 20. It is seen that an opening 22 is provided at the bottom of the container 12 to permit vapor to enter the container from a source of reactant fluid which may be water 24 located in a boat 26.

Energy for operating the sterilizer may be supplied via a flexible cord or cable 27 which may be connected to an alternating current or direct current power source from either a fixed site or a mobile source. In a mobile source embodiment the power source may be the vehicular electrical system. This has particular advantages in areas where sources of electrical energy are not available. Thus in mobile medical units the vehicle battery supply and charging system can be employed to power the sterilizer. A power converter 28 is used to provide both the high voltage and the filament power to a microwave source which may be a magnetron 30 operating at a suitable frequency permitted in the industrial, scientific and medical bands usually at 915 MHz, 2450 MHz, or 5800 MHz. In a preferred embodiment the microwave source magnetron operates at a center frequency of 2450 MHz. An output probe 32 of the magnetron extends into the closed end of a wave guide 34 to launch microwave energy within the wave guide at the dominant mode depending upon the geometry of the guide.

It is understood that the position of the magnetron probe and size of the waveguide is chosen to transmit only the dominant mode without any attenuation. Higher order modes are beyond the cutoff wavelength of the waveguide and are therefore attenuated.

The wave guide may take various forms and in the embodiment shown is cylindrical and secured to the chamber 12 by being screwthreaded to a flange 36 that depends from the bottom of the chamber.

Figure 5:
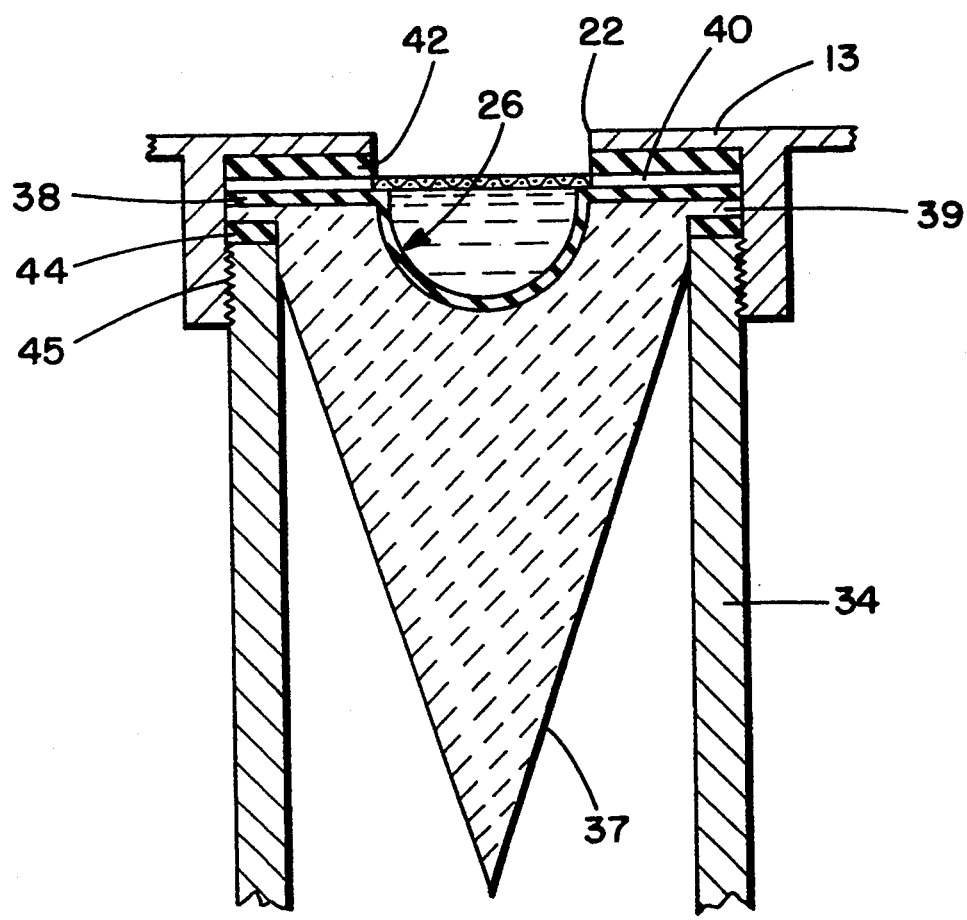
FIG. 5 is a detail view of the structure joining the waveguide to the sterilization chamber.

Located within the wave guide is a tapered dielectric 37 which may be made of a ceramic or a high temperature synthetic material and that serves as an impedance matching device. The dielectric in the embodiment shown is conically shaped having a depression or cavity in its base to receive the boat 26. The dieletric base has an outwardly extending flange 39 that overlays the upper edge of the open end of the wave guide 34. The gasket 44 positioned between the flange 39 and the end of waveguide 34 provides a seal as seen more clearly in FIG. 5. The outer extension 38 of boat 26 overlays the upper base of member 37 and a metal termination plate 40 is positioned between the boat and chamber cylinder 13. A second sealing gasket 42 is located at the perimeter of the top surface of the terminating plate 40 to prevent leakage of gases or vapors of the chamber 12 into the wave guide 34. As seen in FIG. 3 the termination plate 40 includes perforations or a screen 46 that coincides with the upper opening 48 of boat 26 and the opening 22 in chamber 12. Thus as the fluid 24 in the boat vaporizes the vapors will pass through perforations 46 and opening 22 into the interior of the chamber.

The entire coupling assembly of gaskets 42, 44, dielectric 37, boat 26 and terminating plate 40 are tightly secured in place by the screw threaded end of waveguide 34 mating with the internal threads 45 in the flange 36 depending from chamber cylinder 13. It is, of course, realized that alternative coupling arrangments could be used to maintain this assembly in place in a vapor tight manner.

A particularly important feature in the present design is that there is an efficient electrical coupling between the microwave energy and the supply of reactant liquid resulting in a rapid and efficient vaporization of the liquid. This feature includes the conically tapered dielectric 37 serving as the impedance matching device between the characteristic impedance of the wave guide and the metal termination plate 40. The termination plate presents an electrical short circuit at the end of the wave guide 34 and the gradual taper of Unit 37 permits all of the power from the microwave source to be delivered to the liquid 24 with almost none of the energy reflected back to the source. This provides the highly efficient microwave energy coupling to the liquid thus permitting the use of a lower power source.

It is realized that the tapered dielectic 37 may take various configurations and dimensions within the scope of the present invention. The important functional feature is the matching of the impedance of the waveguide 34 to the coupling structure 37 to minimize microwave reflections and maximize energy absorption by the reactant liquid 34. Thus the taper is related in a harmonic manner to the wavelength of the microwave energy. In the present embodiment, the taper is conical and one wavelength in length at 2450 MHz.

It should further be understood that the cavity in the dielectic base may be of various shapes to contain the liquid. The boat 26 serves as a liner for the cavity in dielectic 37 which serves as a container or reservoir for the reactant fluid 24.

The microwave source and cavity is designed as a closed loop system for optimum operation and efficient use of energy. Thus, a detector 50 is positioned within chamber 12 and continually monitors a parameter of the vapor environment within the chamber such as pressure or temperature or both. Detector 50 feeds to the power converter 28 by line 52 and serves to control the converter in accordance with the vapor requirements of the chamber. This closed loop arrangement is completed by the evaporation of the liquid and its subsequent condensation and reflow back to the liquid source 24. As a result, an optimum continuous sterilization system is provided.

Having thus described the invention with particular reference to the preferred forms thereof, it will be obvious that various changes and modifications may be made therein without departing from the spirit and scope of the invention as defined in the appended claims.

What is claimed is:

1. A device for sterilizing objects including medical and dental instruments comprising:
    a walled hollow chamber constructed to receive objects to be sterilized;
    said chamber having an opening in the wall thereof;
    container means located adjacent the chamber wall at the opening thereof and constructed to receive a liquid reactant;
    a waveguide having an open end and a closed end;
    means to secure the waveguide open end to the chamber at the opening thereof;
    a source of microwave energy;
    means connecting said source of microwave energy to the said waveguide;
    impedance matching mechanical means located within said waveguide to couple said waveguide to said container means; and
    metallic plate means having openings therein in contact with the open end of the waveguide whereby substantially all of the microwave energy from the microwave source is absorbed by the reactant liquid in said container means and is prevented from entering the chamber.

2. The device set forth in claim 1 in which said area openings are positioned over the container means to permit vapor from the container means to enter the hollow chamber.

3. The device set forth in claim 2 in which the openings in the metallic plate means comprises a screen.

4. The device set forth in claim 2 in which the openings in the metallic plate means comprises perforations passing through the plate.

5. A device for sterilizing objects by steam at high pressure and temperature comprising;
    a hollow walled chamber constructed to receive objects to be sterilized;
    said chamber having an opening in the wall thereof;
    a elongated waveguide having an open end and a closed end;
    tapered means having a base surface located within the elongated waveguide;
    said tapered means being secured to the hollow chamber with said base surface adjacent the chamber opening and the tapered means located outside the chamber;
    said base surface having a cavity formed therein providing a liquid container means;
    a source of microwave energy;
    means connecting said source of microwave energy to said waveguide; and
    said tapered means serving to match the impedance of the waveguide to the liquid container means whereby substantially all of the microwave energy from the microwave source is absorbed by liquid in the container means.

6. The device set forth in claim 5 including:
    liner means located within said cavity formed in the base surface of the tapered means and metal plate means with holes therein positioned between the open end of the waveguide and the opening in said chamber.

7. The device set forth in claim 5 including
    detector means positioned in said chamber; and
    means connecting the detector means to the source of microwave energy to control said microwave energy to the fluid in the container means.

8. A system for coupling a source of microwave energy to a supply of liquid to maximize the absorption of microwave energy by said liquid comprising;
    a elongated waveguide;
    tapered means located within said waveguide and having a base surface;
    a cavity in said base surface forming a liquid container means;
    metallic plate means covering said liquid container means;
    said metallic plate means having openings to permit vapor from liquid within the container means to pass out of the container means; and
    said tapered means having a width and length to match the impedance of the waveguide and the liquid container means and metallic plate means.

* * * * *